United States Patent [19]

Robinson et al.

[11] Patent Number: 4,990,627

[45] Date of Patent: Feb. 5, 1991

[54] POLYETHERIMIDES AND THEIR PRODUCTION

[75] Inventors: Gene C. Robinson; G. Patrick Stahly, both of Baton Rouge, La.

[73] Assignee: Ethyl Corporation, Richmond, Va.

[21] Appl. No.: 290,583

[22] Filed: Dec. 27, 1988

[51] Int. Cl.$^5$ ............................................ C07D 209/48
[52] U.S. Cl. ............................... 548/473; 546/316; 548/476
[58] Field of Search ....................... 548/472, 473, 476; 528/170; 568/722; 546/316

[56] References Cited

U.S. PATENT DOCUMENTS 4,206,076 6/1980 Hofer et al. .......................... 548/476
4,455,431 6/1984 Williams, III et al. ............. 548/461

Primary Examiner—Mukund J. Shah
Assistant Examiner—D. D. Cair
Attorney, Agent, or Firm—Richard J. Hammond; John F. Sieberth

[57] ABSTRACT

The polyetherimides have repeating groups which may be represented by the general formula:

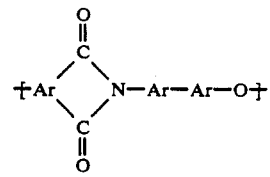

They are produced from novel monomers of the formula

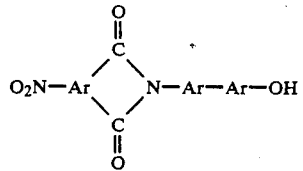

Synthesis procedures for forming such monomers are also described.

6 Claims, No Drawings

POLYETHERIMIDES AND THEIR PRODUCTION

TECHNICAL FIELD

This invention relates to polyetherimides, to methods for the production of such polymers, and to novel compounds useful, inter alia, as intermediates for the synthesis of such polymers

THE INVENTION

In accordance with this invention there is provided a new class of polyetherimides having repeating groups which may be represented by the general formula:

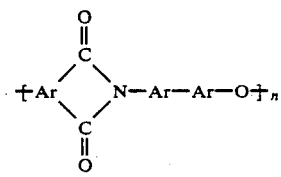
(I)

wherein each Ar is an aromatic group, which may contain 24 or more carbon atoms but which ordinarily will contain no more than about 18 carbon atoms. One, any two, or all three of the aromatic groups depicted in Formula I above may be substituted or unsubstituted aromatic groups. The divalent aromatic groups (i.e., those bonded directly to each other) are preferably substituted or most preferably unsubstituted 1,4-phenylene groups, but may also be substituted or unsubstituted 4,4'-biphenylene groups, substituted or unsubstituted 1,4-naphthylene groups, substituted or unsubstituted 1,5-naphthylene groups, substituted or unsubstituted 4,4''-terphenylene groups, and the like, in which the substituents, if present, may be on the same or different aromatic rings, and are alkyl, haloalkyl, alkoxy, cycloalkyl, aryl, aralkyl, halo, mercapto, alkylthio, arylthio, and like substituents. Such substituents may be present on the trivalent aromatic group (i.e., the group bonded directly to two carbonyl groups and to an oxygen atom of an adjacent repeating unit), either in lieu of, or in addition to, substitution on one or both of the divalent aromatic groups. It is important that the substituents not be such as to interfere with the formation and stability of the polymer, and thus the ring substituents will normally be relatively small such that they do not prevent the polymerization because of steric hindrance.

The polymers of this invention may be prepared by polymerization of a monomer which may be represented by the following fundamental formula:

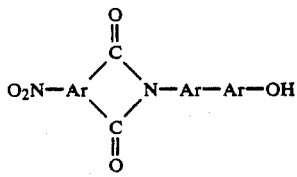
(II)

where the groups designated Ar are, independently, substituted or unsubstituted (except for substituents depicted) aromatic groups such as are described above. Exemplary compounds of Formula II above include the following:

N-[4'-(4'-hydroxy-1,1'-biphenylyl)]-3-nitrophthalimide
N-[4-(3'-ethyl-4'-hydroxy-1,1'-biphenylyl)]-3-nitrophthalimide
N-[4-(3',5'-difluoro-4'-hydroxy-1,1'-biphenylyl)]-3-nitrophthalimide
N-[4-(4'-hydroxy-1,1'-biphenylyl)]-4-nitrophthalimide
N-[4-(3'-ethyl-4'-hydroxy-1,1'-biphenylyl)-4-nitrophthalimide
N-[4-(3',5'-difluoro-4'-hydroxy-1,1'-biphenylyl)]-4-nitrophthalimide
N-[4-(4'-hydroxy-1,1'-biphenylyl)]-5-methyl-4-nitrophthalimide
N-[4-(3',5'-diisopropyl-4'-hydroxy-1,1'-biphenylyl)]-4-nitrophthalimide
N-[4-(3',5'-di-tert-butyl-4'-hydroxy-1,1'-biphenylyl)]-4-nitrophthalimide
N-[4-(4'-hydroxy-1,1'-biphenylyl)]-3-chloro-4-nitrophthalimide
N-[4-(4'-hydroxy-1,1'-biphenylyl)]-3,6-dichloro-4-nitrophthalimide
N-[4-(3',5'-difluoro-4'-hydroxy-1,1'-biphenylyl)]-5-fluoro-4-nitrophthalimide
N-[4-(3'-tert-butyl-4'-hydroxy-5'-methoxy-1,1'-biphenylyl)]-4-nitrophthalimide
N-[4-(4''-hydroxy-1,1''-terphenylyl)]-4-nitrophthalimide
N-[4-(4'-hydroxy-2',3',5'-trimethyl-1,1'-biphenylyl)]-4-nitrophthalimide,
N-[4-(4'-hydroxy-3',5'-trifluoromethyl-1,1'-biphenylyl)]-4-nitrophthalimide
N-[3-(4'-hydroxy-1,1'-biphenylyl)]-4-nitrophthalimide
N-[2-(4'-hydroxy-1,1'-biphenylyl)]-4-nitrophthalimide
N-[4-(2'-hydroxy-1,1'-biphenylyl)]-4-nitrophthalimide
N-[4-(3'-tert-butyl-2'-hydroxy-1,1'-biphenylyl)]-4-nitrophthalimide Compounds of the general class depicted in Formula II constitute another embodiment of this invention.

It will be noted that in some of the above illustrative compounds of Formula II, the hydroxyl group is sterically hindered by one or two relatively bulky groups in the ortho position, such as secondary or tertiary alkyl groups. As will be seen from the ensuing description, such compounds are nonetheless highly suitable as intermediates to the synthesis of the polymers of Formula I above, as the groups contributing the steric hindrance to the hydroxyl group can be removed from the compound of Formula II to facilitate polymerization.

From the standpoint of thermal stability, the preferred polymers of Formula I above are those in which the aromatic groups are all unsubstituted or one or more of them are substituted only with fluorine atoms or perfluoroalkyl groups. In the case of the compounds of Formula II above, the corresponding unsubstituted or fluoro-substituted or perfluoralkyl-substituted compounds are preferred for use as monomers in the polymerization process. However the preferred compounds of Formula II from the standpoint of producing such monomers are those in which the ortho positions relative to the hydroxyl group are both occupied by secondary or, most preferably, tertiary alkyl groups. Such groups can facilitate the synthesis of some of the starting materials (compounds of Formula III below) and are readily dealkylated prior to the polymerization process.

Polymerization of the monomer(s) of Formula II above may be effected by use of the general procedure reported by Williams and Relles in U.S. Pat. No. 4,297,474, which involves preformation of phenoxide ion in toluene or other suitable aromatic solvent followed by thermal polymerization in a dipolar aprotic solvent such as N,N-dimethylformamide, N,N-diethylformamide, N,N-dimethylacetamide, N,N-diethylacetamide, N-methyl-2-pyrrolidone, or the like. The disclosure of the foregoing patent of Williams and Relles is incorporated herein in toto by reference. Other polymerization methods may also be found suitable.

There are at least two routes by which the monomers of Formula II above may be prepared. Both involve use of a nitroaromatic-substituted phenolic compound of the general formula

$$O_2N-Ar-Ar-OH \qquad (III)$$

where the groups designated Ar are, independently, substituted or unsubstituted (except for the nitro and hydroxyl substituents depicted) aromatic groups such as are described above. Exemplary compounds of Formula III above include the following:

4-(2'-nitrophenyl)phenol
4-(3'-nitrophenyl)-2,6-dimethylphenol
4-(3'-nitrophenyl)-2-ethyl-6-methylphenol
4-(3'-nitrophenyl)-2,6-bis(trifluoromethyl)phenol
4-(3'-nitrophenyl)-2,6-dichlorophenol
4-(3'-nitrophenyl)-2-isopropyl-1-naphthol
4-(4'-methyl-3'-nitrophenyl)-2,6-dimethylphenol
4-(3'-nitrophenyl)-2,6-diisopropylphenol
4-(3'-nitrophenyl)-2,6-di-tert-butylphenol
4-(3'-nitrophenyl)-2-chloro-6-methylphenol
4-(4'-nitrophenyl)phenol
4-(4'-nitrophenyl)-2,6-dimethylphenol
4-(4'-nitrophenyl)-2,6-difluorophenol
4-(4'-nitrophenyl)-2-tert-amyl-6-methylphenol
4-(4'-nitrophenyl)-2,6-dibromophenol
4-(6'-methyl-4'-nitrophenyl)phenol
4-(6'-fluoro-4'-nitrophenyl)phenol
4-(2,6'-difluoro-4'-nitrophenyl)phenol
4-(4'-nitro-6'-methoxyphenyl)-2,6-diisopropylphenol
4-(4'-nitrophenyl)-2,6-di-tert-butylphenol
4-(4'-nitrophenyl)-2-chloro-6-methylphenol
4-(4''-nitrobiphenylyl)phenol
4-[(4'''-nitroterphenylyl)phenyl)]phenol
4-(4'-nitrophenyl)-1-naphthol
4-(4'-nitrophenyl)-2-isopropyl-1-naphthol
4-(4'-nitrophenyl)-2-naphthol and similar compounds of this type. Such compounds may be formed by various methods, such as nucleophilic aromatic substitution reactions as described in Wright and Jorgensen, *J. Org. Chem.*, 1968, 33, 1245.

In one preferred synthesis route, the monomers of Formula II above are formed by subjecting a nitroaromatic-substituted phenolic compound of Formula III above to hydrogenation to form an aminoaromatic-substituted phenolic compound of the formula:

$$H_2N-Ar-Ar-OH \qquad (IV)$$

where the groups designated Ar are, independently, substituted or, except for the amino and hydroxyl substituents depicted, unsubstituted aromatic groups such as are described above The aminoaromatic-substituted phenolic compound (Formula IV above) is then imidized by reaction with a nitrophthalic anhydride (which may contain appropriate ring substitution) to produce a compound of Formula II above. Such compound, if the hydroxyl group is not sterically hindered, may then be polymerized such as in the manner described above. If on the other hand the hydroxyl group is hindered by bulky alkyl or like substitution in the ortho position or positions, the compound of Formula II is subjected to a suitable dealkylation process in order to remove such hindering group(s), and then is polymerized as above.

The procedures and conditions for effecting the foregoing transformations from compounds of (III) to (IV) and thence to (II), including the dealkylation of a hindered compound (II) to an unhindered compound (II), are known and reported in the literature. For example:

For converting (III) to (IV), see March, *Advanced Organic Chemistry*, 3rd Edition, Wiley-Interscience, New York, 1985, page 1103;

For converting (IV) to (II), see Williams and Donahue, *J. Org. Chem.*, 1977, 42, 3414;

For dealkylation procedures, see Tashiro, *Synthesis*, 1979, 921.

Each of these publications is incorporated in toto herein by reference.

A second synthesis route for converting the nitroaromatic-substituted phenolic compounds of Formula III above to the monomers of Formula II above involves the same hydrogenation and imidization sequence as described above except that where the hydroxyl group of the nitroaromatic-substituted phenolic compound used is sterically hindered, the dealkylation is performed before proceeding with the hydrogenation and imidization. Thus in this case the resultant product of Formula II above can be directly used in the polymerization. Thus the procedures and reaction conditions for this route are essentially the same as those suitable for use in the first synthesis route described above.

The polymers of this invention can be used for production of films, fibers, membranes, coatings, plaques, foams, laminates, adhesives, composites, tubes, and molded products of various shapes and configurations, the utility in any given case being governed to some extent by the molecular weight and physical properties of the particular polymer at hand. Besides their usefulness in the synthesis of the polymers of this invention, the compounds of Formula II above may be used directly as, or as intermediates for, the synthesis of pesticides, germicides, miticides, acaricides, herbicides, plant growth regulants, and the like. For example, reaction of such compounds with $PCl_3$, $POCl_3$, or $PSCl_3$, yields nitroaromatic phosphites, phosphates, or thionophosphates which can be used as an active ingredient in conventional liquid spray or powder formulations either as insecticides for extermination of flies, mosquitoes, ants, or roaches, or as plant fungicides, or both.

Having described the basic concepts of this invention, reference will now be made to the following specific examples which are illustrative but not limitive of its practice.

Example 1 illustrates the synthesis of a typical nitroaromatic-substituted phenolic compound used as a starting material for the two synthesis routes described above. Examples 2–5 illustrate the first route mentioned above involving the sequence of hydrogenation, imidization, dealkylation and polymerization. The second route described above involves a dealkylation, hydrogenation, imidization, polymerization sequence such as shown in Examples 6, 7, 8 and 5 respectively.

EXAMPLE 1

4-(4'-Nitrophenyl)-2,6-di-tert-butylphenol

A mixture of 12.0 g (300 mmol) of powdered sodium hydroxide, 24.7 g (120 mmol) of 2,6-di-tert-butylphenol, 15.7 g (100 mmol) of 1-chloro-4-nitrobenzene, and 120 mL of DMSO was stirred for 17 hours at 90° C. and poured into one liter of 1N HCl. The resulting aqueous mixture was extracted with three 250 mL portions of diethyl ether. Combination, drying (MgSO$_4$), and concentration of the organic layers afforded a residue which was purified by two recrystallizations from ethanol-dichloromethane to give 22.3 g (68% yield) of 4-(4'-nitrophenyl)-2,6-di-tert-butylphenol which an also be named 3,5-bis-(1,1-dimethylethyl)-4'-nitro-(1,1'-biphenyl)-4-ol.

EXAMPLE 2

4-(4'-Aminophenyl)-2,6-di-tert-butylphenol

A mixture of 5.0 g (15 mmol) of 4-(4'-nitrophenyl)-2,6-di-tert-butylphenol, 0.5 g of 5% palladium on carbon, and 250 mL of absolute ethanol was hydrogenated for one hour under 50 psig of hydrogen, filtered, and concentrated to give 4.7 g (quantitative yield) of 4-(4'-aminophenyl)-2,6-di-tert-butylphenol as a foam: $^1$H NMR (CDCl$_3$) 1.48 (s, 18H), 3.25 (broad s, 2H), 5.20 (broad s, 1H), 6.67 (d, 2H, J=9 Hz), 7.36 (s, 2H), 7.36 (d, 2H, J=9 Hz). This compound may also be named 3,5-bis(1,1-dimethylethyl)-4'-amino-(1,1'-biphenyl)-4-ol.

EXAMPLE 3

N-[4-(3',5'-Di-tert-butyl-4'-hydroxy-1,1'-biphenylyl)]-4-nitrophthalimide

A mixture of 4.7 g (16 mmol) of 4-(4'-aminophenyl)-2,6-di-tert-butylphenol, 3.1 g (16 mmol) of 4-nitrophthalic anhydride, and 40 mL of glacial acetic acid was heated at 100°-110° C. overnight, allowed to cool to ambient temperature, and poured into 200 mL of water. The resulting aqueous mixture was extracted with two 100-mL portions of dichloromethane. The organic layers were combined, washed with two 100-mL portions of water, dried (MgSO$_4$), and concentrated to give a residue which was crystallized from dichloromethane-hexane, affording 6.3 g (83% yield) of yellow N-[4-(3',5'-di-tert-butyl-4'-hydroxy-1,1'-biphenylyl)]-4-nitrophthalimide: $^1$H NMR (CDCl$_3$) 1.51 (s, 18H), 5.32 (s, 1H), 7.46 (s, 2H), 7.60 (AB, 4H), 8.19 (d, 1H, J=9 Hz), 8.60-8.90 (m, 2H); IR (KBr) 3640, 2980, 1735, 1550, 1440, 1390, 1350 cm$^{-1}$.

EXAMPLE 4

N-[4-(4'-Hydroxy-1,1'-biphenylyl)]-4-nitrophthalimide

To a solution of 4.2 g (8.9 mmol) of N-[4-(3',5'-di-tert-butyl-4'-hydroxy-1,1'-biphenylyl)]-4-nitrophthalimide in 100 mL of toluene was added a solution of 5.3 g (40 mmol) of aluminum chloride in 15 mL of nitromethane. This mixture was stirred at ambient temperature for 4 hours and poured into 400 mL of 1N HCl. The resulting yellow, crystalline solid was removed by filtration, triturated with 200 mL of refluxing ethyl acetate, and dried in vacuo to give 3.7 g of material. Recrystallization of this from pyridine afforded 1.8 g (56% yield) of orange-colored N-[4-(4'-hydroxy-1,1'-biphenylyl)]-4-nitrophthalimide: mp 300° C.; $^1$H NMR (DMSO-d$_6$) 6.89 (d, 2H), 7.50 (d, 2H), 7.56 (d, 2H), 7.75 (d, 2H), 8.21 (d, 1H), 8.60 (d, 1H), 8.70 (dd, 1H); IR (KBr) 3460, 3100, 1725, 1545, 1510, 1400, 1350 cm$^{-1}$.

EXAMPLE 5

Polyetherimide Production

A slurry of 1.0 g (2.8 mmol) of imide N-[4-(4'-hydroxy-1,1'-biphenylyl)]-4-nitrophthalimide in 5 mL of toluene was treated with 0.31 g (2.8 mmol) of potassium tert-butoxide and stirred vigorously at ambient temperature for one hour. Addition of 10 mL of DMF to the dark brown slurry afforded a solution, which was heated at 80° C. for 3 hours and poured into 100 mL of methanol containing 0.5 mL of 37% HCl. The resulting precipitate was collected by filtration and dried in vacuo to afford 0.86 g of light tan polyetherimide: IR (KBr) 3470 (water ?), 3100, 1730, 1505, 1380, 1280, 1245 cm$^{-1}$; intrinsic viscosity (NMP, 100° C.) 0.03-0.07; differential scanning calorimetry, scan 1 transitions −16° C., 43° C., scan 2 transition 22° C. The polymer contains repeating units of the formula

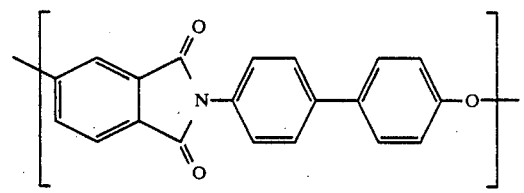

EXAMPLE 6

4-(4'-Nitrophenyl)phenol

To a solution of 5.0 g (15 mmol) of 4-(4'nitrophenyl)-2,6-di-tert-butylphenol in 50 mL of toluene was added a solution of 9.2 g (69 mmol) of aluminum chloride in 10 mL of nitromethane. This mixture was stirred at ambient temperature for 4 hours and poured into 100 mL of 1N HCl mixed with ice. The resulting aqueous mixture was extracted with two 100-mL portions of ethyl acetate. Combination, drying (MgSO$_4$), and concentration of the organic layers resulted in crystallization of 2.3 g (69% yield) of yellow 4-(4'-nitrophenyl)phenol, which may also be named as 4'-nitro-(1,1'-biphenyl)-4-ol: $^1$H NMR (DMSO-d$_6$) 6.93 (d, 2H, J=9 Hz), 7.64 (d, 2H, J=9 Hz), 7.82 (d, 2H, J=9 Hz), 8.25 (d, 2H, J=9 Hz), 9.98 (broad s, 1H).

EXAMPLE 7

4-(4'-Aminophenyl)phenol

This compound, also known as 4,-amino-(1,1'-biphenyl)-4-ol, was formed from 4'(4'-nitrophenyl)-phenol using the hydrogenation procedure described in Example 2.

EXAMPLE 8

N-[4-(4-Hydroxy-1,1'-biphenylyl]-4-nitrophthalimide

The procedure of Example 3 was applied to an equivalent quantity of 4-(4'-aminophenyl)phenol in lieu of 4-(4'-aminophenyl)-2,6-di-tert-butylphenol.

The above disclosure has been presented for purposes of illustration and not limitation. As can readily be appreciated by those skilled in the art, this invention is susceptible to considerable variation in its practice within the spirit and scope of the ensuing claims.

What is claimed is:

1. A compound of the formula

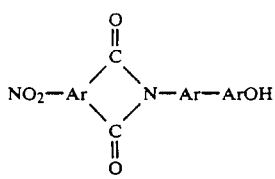

wherein the groups —Ar—Ar— are unsubstituted or substituted 1-4-phenylene; unsubstituted or substituted 4,4'-biphenylene; unsubstituted or substituted 1,4-naphthylene; unsubstituted or substituted 1,5-naphthylene; or unsubstituted or substituted 4,4'-terphenylene the substituents on the same or different rings of said group —AR—AR and are alkyl, haloalkyl, alkoxy, cycloalkoxy, aryl, halo, aralkyl, mercapto, alkylthio, or arylthio and the group AR—NO$_2$ is phenyl unsubstituted or substituted with alkyl, haloalkyl, alkoxy, cycloalkoxy, aryl, halo, aralykyl, mercapto, alkylthio or arylthio.

2. A compound of the formula:

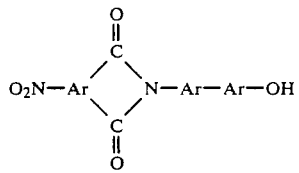
(II)

wherein each Ar depicted is an aromatic group having up to about 24 carbon atoms.

3. A compound of claim 2 wherein each of the two Ar groups bonded directly to each other is a phenylene group of the formula C$_6$H$_4$.

4. A compound of claim 2 wherein each of the two Ar groups bonded directly to each other is a 1,4-phenylene group of the formula C$_6$H$_4$.

5. N-[4-(3',5'-di-tert-butyl-4'-hydroxy-1,1'-biphenylyl)]-4-nitrophthalimide.

6. N-[4-(4'-hydroxy-1,1'-biphenylyl)]-4-nitrophthalimide.

* * * * *